(12) United States Patent
Qiu et al.

(10) Patent No.: US 9,303,060 B1
(45) Date of Patent: Apr. 5, 2016

(54) METHODS OF PREPARING INTERMEDIATE OF FLUTICASONE PROPIONATE

(71) Applicant: AMPHASTAR PHARMACEUTICALS INC., Rancho Cucamonga, CA (US)

(72) Inventors: Yinhua Qiu, Nanjing (CN); Zhengyuan Wu, Nanjing (CN); Yong Liu, Nanjing (CN); Song Chen, Nanjing (CN); Haoning Zhang, Nanjing (CN)

(73) Assignee: Amphaster Pharmaceuticals, Inc., Rancho Cucamonga, CA (US)

( * ) Notice: Subject to any disclaimer, the term of this patent is extended or adjusted under 35 U.S.C. 154(b) by 0 days.

(21) Appl. No.: 14/688,960

(22) Filed: Apr. 16, 2015

Related U.S. Application Data

(60) Provisional application No. 62/059,786, filed on Oct. 3, 2014.

(51) Int. Cl.
*C07J 31/00* (2006.01)

(52) U.S. Cl.
CPC ..................... *C07J 31/006* (2013.01)

(58) Field of Classification Search
CPC ................. C07J 31/006; C07J 75/00
See application file for complete search history.

(56) References Cited

U.S. PATENT DOCUMENTS

| 4,335,121 | A | 6/1982 | Phillipps et al. |
| 8,344,168 | B2 | 1/2013 | Gore et al. |
| 8,841,442 | B2 * | 9/2014 | Solanki et al. ............... 540/114 |
| 2006/0009435 | A1 | 1/2006 | Kaspi et al. |
| 2007/0270584 | A1 | 11/2007 | Loevli et al. |

FOREIGN PATENT DOCUMENTS

| EP | 1431305 A1 | 6/2004 |
| IN | WO 2012/029077 A2 * | 3/2012 |
| WO | WO 01/62722 A2 | 8/2001 |
| WO | WO 2004/001369 A2 | 12/2003 |
| WO | WO 2004/052912 A1 | 6/2004 |
| WO | WO 2007/012228 A1 | 2/2007 |

* cited by examiner

*Primary Examiner* — Paul A Zucker
(74) *Attorney, Agent, or Firm* — Lewis Roca Rothgerber Christie LLP

(57) ABSTRACT

A method of preparing a thioic acid intermediate of fluticasone propionate includes: treating a 17β-[(N,N-dimethyl carbamoyl)thio]carbonyl compound in a solution including an alcohol and an alkali metal hydroxide, an alkaline-earth metal hydroxide, or a mixture thereof to cleave an amide from the 17β-[(N,N-dimethyl carbamoyl)thio]carbonyl compound; treating the solution to separate an aqueous portion; and adding an acid to the aqueous portion to obtain the thioic acid intermediate of fluticasone propionate. A method of preparing fluticasone propionate includes preparing the thioic acid intermediate of fluticasone propionate, and alkylating the thioic acid intermediate of fluticasone propionate to prepare the fluticasone propionate.

24 Claims, 2 Drawing Sheets

Compound 4

Compound 1

Fluticasone Propionate

METHODS OF PREPARING INTERMEDIATE OF FLUTICASONE PROPIONATE

CROSS-REFERENCE TO RELATED APPLICATION

This application claims priority to and the benefit of related U.S. Provisional Application Ser. No. 62/059,786, filed in the U.S. Patent and Trademark Office on Oct. 3, 2014, the entire content of which is incorporated herein by reference.

BACKGROUND

The structure of fluticasone propionate is illustrated as follows:

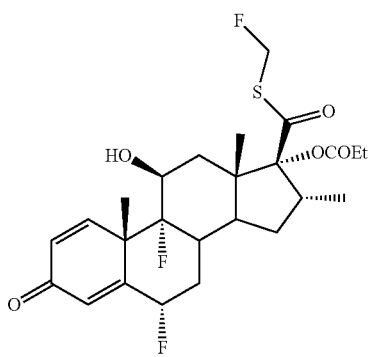

6α,9α-difluoro-11β-hydroxy-16α-methyl-3-oxo-17α-propionyloxyandrosta-1,4-diene-17β-carbothioate (Compound 1) is utilized as an intermediate (or a key or important intermediate) in the synthesis of fluticasone propionate. The structure of Compound 1 is illustrated as follows:

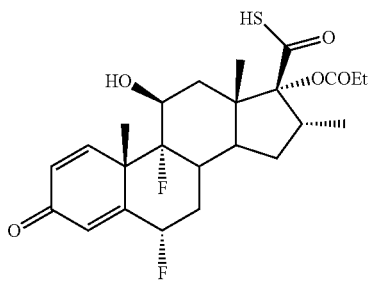

6α,9α-difluoro-11β-hydroxy-16α-methyl-3-oxo-17α-propionyloxyandrosta-1,4-diene-17β-carbothioate
(Compound 1)

Fluticasone propionate may be synthesized by way of the oxidation of flumethasone to yield Compound 1, which may be reacted to obtain fluticasone propionate. The synthetic route for the foregoing synthesis may be generally illustrated as shown in FIG. 1.

Dimethylthiocarbamoyl chloride may be used as a sulfation agent in the above-identified process. Then, the resultant product may be decomposed by refluxing to obtain diethylamine and the thioic acid, Compound 1. However, pollution is generated by that method due, at least in part, to the relatively high consumption of reagents. Additionally, the yield obtained by using diethylamine is low. Diethylamine may also be used as a decomposing agent, but the generation of pollution and low yield have also been observed when diethylamine is used as the decomposing agent.

To facilitate the discussion of the subject matter disclosed herein, Compound 2 is defined herein as 6α,9α-difluoro-11β-hydroxy-16α-methyl-3-oxoandrosta-1,4-diene-17β-carboxylic acid, Compound 3 is defined herein as 6α,9α-difluoro-11β-hydroxy-16α-methyl-3-oxo-17α-propionyloxyandrosta-1,4-diene-17β-carboxylic acid, and Compound 4 is defined herein as 17β-[(N,N-dimethyl carbamoyl)thio]carbonyl-6α,9α-difluoro-11β-hydroxy-16α-methyl-3-oxo-17α-propionyloxyandrosta-1,4-diene. Compounds 2-4 are illustrated as follows:

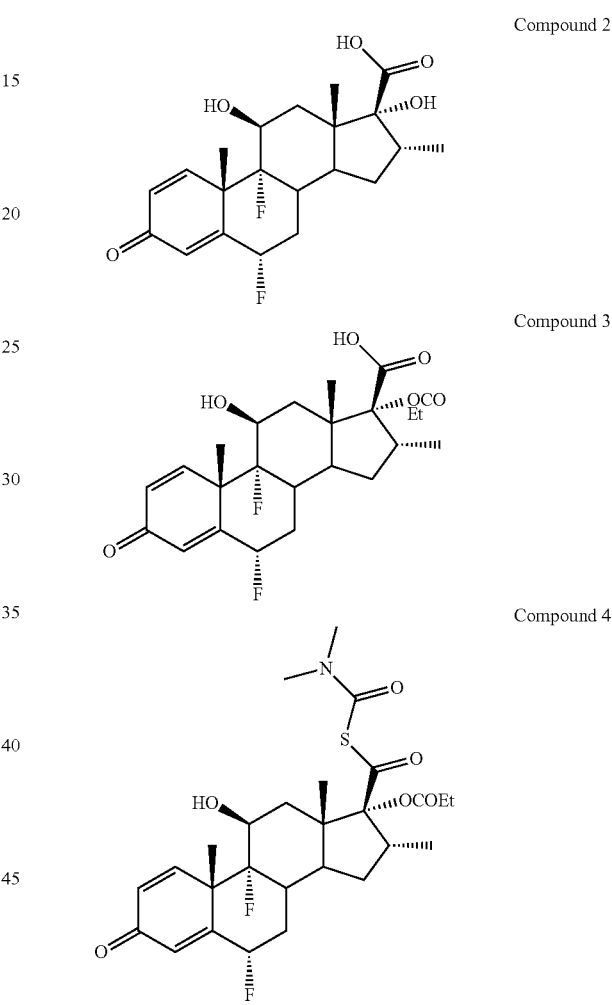

Compound 1 may be generated by reacting Compound 3 with dimethylthiocarbamoyl chloride and sodium iodide in 2-butanaone to obtain Compound 4, which may then be reacted with a hydrolyzing agent, such as sodium hydrosulfide or sodium thiomethoxide, to generate the sodium salt of Compound 1. The sodium salt of Compound 1 may be alkylated in-situ with chlorofluoromethane to yield fluticasone propionate, or the sodium salt of Compound 1 may be acidified to obtain Compound 1, which may also be isolated and converted to fluticasone propionate by alkylation with chlorofluoromethane. When Compound 4 is hydrolyzed by utilizing sodium hydrosulfide or sodium thiomethoxide, however, excess sodium hydrosulfide or sodium thiomethoxide may generate toxic hydrogen sulfide or methyl mercaptan. If the alkylation of the sodium salt of Compound 1 is direct, excess sodium hydrosulfide may react with chlorofluoromethane, and thus, more chlorofluoromethane may be required (e.g., to compensate for the chlorofluoromethane that reacts with the excess sodium hydrosulfide). Further, the resultant impurity of such processes is difficult to remove, thereby affecting (or reducing) the quality (or purity) of the final product.

SUMMARY

Aspects of embodiments of the present disclosure generally relate to a process for the preparation of a reaction intermediate of fluticasone propionate. An embodiment of the reaction intermediate includes 6α,9α-difluoro-11β-hydroxy-16α-methyl-3-oxo-17α-propionyloxyandrosta-1,4-diene-17β-carbothioate. Fluticasone propionate is a corticosteroid derived from fluticasone and may be used to treat asthma and allergic rhinitis. Fluticasone propionate may also be used to treat eosinophilic esophagitis.

According to an embodiment of the present disclosure, a method of preparing a thioic acid intermediate of fluticasone propionate includes: treating a 17β-[(N,N-dimethyl carbamoyl)thio]carbonyl compound in a solution including an alcohol and an alkali metal hydroxide, an alkaline-earth metal hydroxide, or a mixture thereof to cleave an amide from the 17β-[(N,N-dimethyl carbamoyl)thio]carbonyl compound; treating the solution to separate an aqueous portion; and adding an acid to the aqueous portion to obtain the thioic acid intermediate of fluticasone propionate.

The thioic acid intermediate of fluticasone propionate may include Compound 1, 6α,9α-difluoro-11β-hydroxy-16α-methyl-3-oxo-17α-propionyloxyandrosta-1,4-diene-17β-carbothioate, or a derivative thereof:

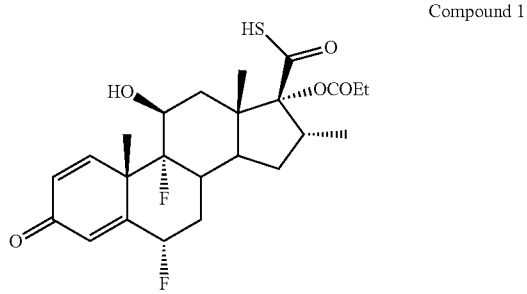

Compound 1

The 17β-[(N,N-dimethyl carbamoyl)thio]carbonyl compound may include Compound 4, 17β-[(N,N-dimethylcarbamoyl)thio]carbonyl-6α,9α-difluoro11β-hydroxy-16α-methyl-3-oxo-17α-propionyloxyandrosta-1,4-diene, or a derivative thereof:

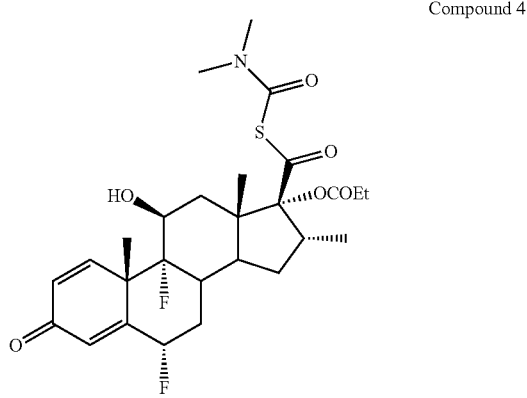

Compound 4

The treating of the solution may remove impurities and may include evaporating at least a portion of the alcohol from the solution, adding water and an organic solvent, and stirring to separate the aqueous portion from the solution.

The adding of the acid may include adding the acid dropwise to the aqueous portion.

The alkali metal hydroxide may include lithium hydroxide, sodium hydroxide, potassium hydroxide, or a mixture thereof, and the alkaline-earth metal hydroxide may include magnesium hydroxide, calcium hydroxide, or a mixture thereof.

The alkali metal hydroxide may include sodium hydroxide, and the alkaline-earth metal hydroxide may include calcium hydroxide.

A mole ratio of the total amount of the alkali metal hydroxide and the alkaline-earth metal hydroxide to the amount of the 17β-[(N,N-dimethyl carbamoyl)thio]carbonyl compound may be about 1:1 to about 5:1.

The mole ratio of the total amount of the alkali metal hydroxide and the alkaline-earth metal hydroxide to the amount of the 17β-[(N,N-dimethyl carbamoyl)thio]carbonyl compound may be about 1.5:1.

The alcohol may include methanol, ethanol, propanol, butanol, or a mixture thereof.

The alcohol may include methanol.

A volume to weight ratio of the alcohol to the 17β-[(N,N-dimethyl carbamoyl)thio]carbonyl compound may be about 5:1 to 30:1 v/w.

The volume to weight ratio of the alcohol to the 17β-[(N,N-dimethyl carbamoyl)thio]carbonyl compound may be about 15:1 v/w.

The treating of the 17β-[(N,N-dimethyl carbamoyl)thio] carbonyl compound may be performed at a reaction temperature of about 0° C. to about 50° C.

The reaction temperature may be about 25° C. to about 30° C.

The organic solvent may include an ester, an ether, an alkane, an aromatic hydrocarbon, a halohydrocarbon, or a mixture thereof.

The ester may include ethyl acetate, methyl acetate, butyl acetate, or a mixture thereof.

The ether may include diethyl ether, methyl tert butyl ether, or a mixture thereof.

The organic solvent may include toluene, dichloromethane, chloroform, or a mixture thereof.

The aromatic hydrocarbon may include toluene.

The acid may include an organic acid, an inorganic acid, or a mixture thereof.

The inorganic acid may include hydrochloric acid, phosphoric acid, sulphuric acid, or a mixture thereof, and the organic acid may include acetic acid, formic acid, propionic acid, or a mixture thereof.

The acid may be added to the aqueous portion to obtain a pH of 1 to 5.

The pH may be 2 to 3.

A method of preparing fluticasone propionate includes: preparing the thioic acid intermediate of fluticasone propionate; and alkylating the thioic acid intermediate of fluticasone propionate to prepare the fluticasone propionate. The alkylating of the thioic acid intermediate of fluticasone propionate may include alkylating the thioic acid intermediate of fluticasone propionate with a halohydrocarbon. The halohydrocarbon may include a chlorofluorocarbon. The chlorofluorocarbon may include chlorofluoromethane.

DETAILED DESCRIPTION

Figure 1:
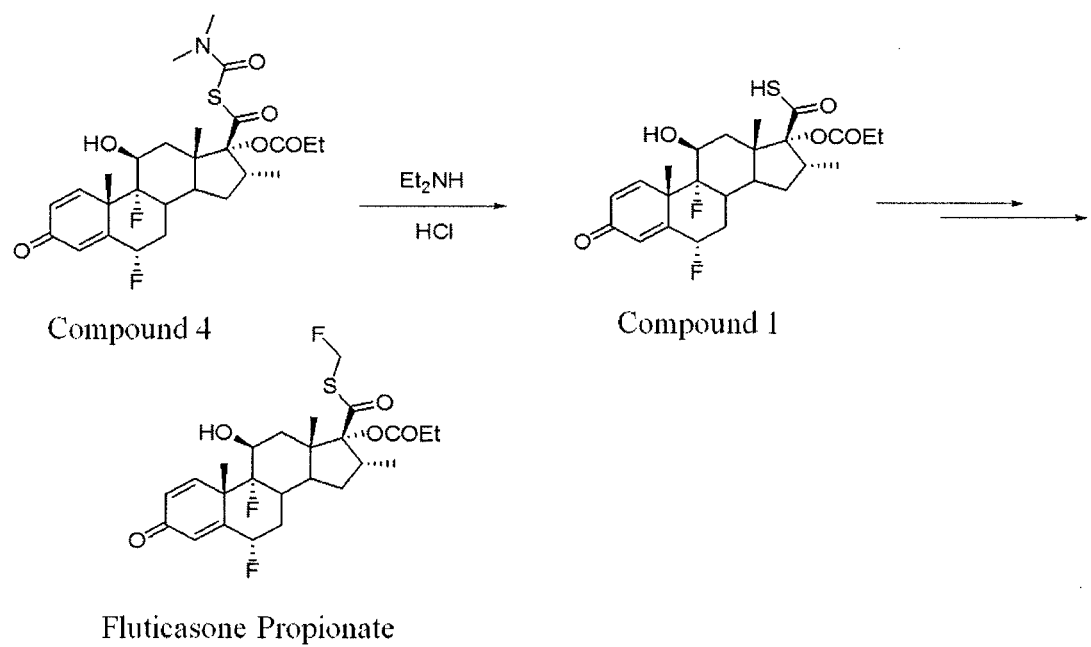
FIG. 1 is a reaction scheme illustrating the oxidation of flumethasone to yield Compound 1.

The following detailed description is provided only for purposes of illustration of embodiments of the present disclosure and not for purposes of limiting the scope of the present invention. Alternate embodiments will be readily apparent to those of skill in the art and are intended to be included within the scope of the present invention. Also, in the context of the present application, the term "thioic acid intermediate of fluticasone propionate" is used in a broad sense and encompasses any thioic acid intermediate that can be used to form fluticasone propionate. For example, as used herein, the term "thioic acid intermediate of fluticasone propionate" encompasses Compound 1 and derivatives thereof (e.g., substituted 6α,9α-difluoro-11β-hydroxy-16α-methyl-3-oxo-17α-propionyloxyandrosta-1,4-diene-17β-carbothioate). As used in the context of the present application, the term "17β-[(N,N-dimethyl carbamoyl)thio]carbonyl compound" is used in a broad sense and encompasses any 17β-[(N,N-dimethyl carbamoyl)thio]carbonyl compound that can be used to form the thioic acid intermediate of fluticasone propionate. For example, as used herein, the term "17β-[(N,N-dimethyl carbamoyl)thio]carbonyl compound" encompasses Compound 4 and derivatives thereof (e.g., substituted 17β-[(N,N-dimethyl carbamoyl)thio]carbonyl-6α,9α-difluoro-11β-hydroxy-16α-methyl-3-oxo-17α-propionyl oxyandrosta-1,4-diene).

Embodiments of the present disclosure provide a facile, efficient, economical, and simple to industrialize process for producing an intermediate (or a key or important intermediate) of fluticasone propionate. The intermediate may include a thioic acid intermediate of fluticasone propionate including Compound 1 (6α,9α-difluoro-11β-hydroxy-16α-methyl-3-oxo-17α-propionyloxyandrosta-1,4-diene-17β-carbothioate). Embodiments of the process provide an improved yield and a highly purified product including the thioic acid intermediate of fluticasone propionate (e.g., Compound 1). For example, according to embodiments of the present disclosure, the percent yield of Compound 1 is improved from 45% to 90%, and the purity of Compound 1 is >98%. Compound 1 is utilized as an intermediate product (e.g., a reaction intermediate) in embodiments of a process of preparing fluticasone propionate. Compound 1 is illustrated as follows:

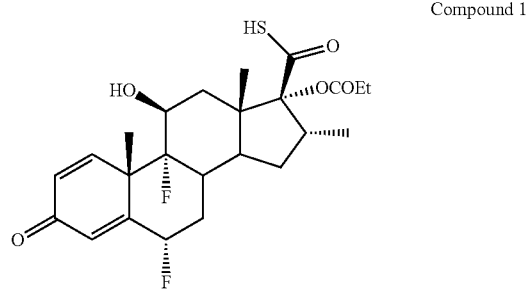

Compound 1

According to an embodiment of the present disclosure, the method of preparing a thioic acid intermediate of fluticasone propionate includes: treating a 17β-[(N,N-dimethyl carbamoyl)thio]carbonyl compound (e.g., Compound 4, 17β-[(N,N-dimethylcarbamoyl)thio]carbonyl-6α,9α-difluoro-11β-hydroxy-16α-methyl-3-oxo-17α-propionyl oxyandrosta-1,4-diene or a derivative thereof) in a solution including an alcohol and an alkali metal hydroxide, an alkaline-earth metal hydroxide, or a mixture thereof to cleave an amide from the 17β-[(N,N-dimethyl carbamoyl)thio]carbonyl compound; treating the solution to separate an aqueous portion, and adding an acid to the aqueous portion to obtain the thioic acid intermediate of fluticasone propionate (e.g., Compound 1, 6α,9α-difluoro-11β-hydroxy-16α-methyl-3-oxo-17α-propionyl oxyandrosta-1,4-diene-17β-carbothioate, or a derivative thereof). The amide may be cleaved from the 17β-[(N,N-dimethyl carbamoyl)thio]carbonyl compound by hydrolysis. The amide may include, for example, $(CH_3)_2NCOOH$. The treating of the solution may remove impurities and may be followed by acid precipitation of the thioic acid intermediate of fluticasone propionate. The adding of the acid may include adding the acid dropwise (e.g., adding droplets of the acid) to the aqueous portion. Embodiments of the present disclosure are convenient and environmental friendly, and produce a final product having high yield and high purity.

For example, according to embodiments of the present disclosure a process of preparing Compound 1 includes: (a) treating Compound 4 (i.e., 17β-[(N,N-dimethyl carbamoyl)thio]carbonyl-6α,9α-difluoro-11β-hydroxy-16α-methyl-3-oxo-17α-propionyl oxyandrosta-1,4-diene) in an alkali metal hydroxide/alcohol or an alkaline-earth metal hydroxide/alcohol to decompose amide (e.g., to cleave an amide from Compound 4); (b) evaporating alcohol, adding water and organic solvent, stirring (e.g., stirring thoroughly), obtaining a water phase (e.g., an aqueous solution or aqueous portion) after removing impurities; (c) obtaining Compound 1 (6α,9α-difluoro-11β-hydroxy-16α-methyl-3-oxo-17α-propionyloxyandrosta-1,4-diene-17β-carbothioate) by adding an acid (e.g., droplets of the acid) to the aqueous solution. The organic solvent may include any suitable organic solvent, such as an ester, an ether, an alkane, an aromatic hydrocarbon, a halohydrocarbon, or a mixture thereof. For example, the ester may include ethyl acetate, methyl acetate, butyl acetate, or a mixture thereof. The ether may include diethyl ether, methyl tert butyl ether, or a mixture thereof. The organic solvent may include the halohydrocarbon (e.g., dichloromethane, chloroform, or a mixture thereof), the aromatic hydrocarbon (e.g., toluene), or a mixture thereof.

The alkali metal hydroxide may include lithium hydroxide, sodium hydroxide, potassium hydroxide, or a mixture thereof, and the alkaline-earth metal hydroxide may include magnesium hydroxide, calcium hydroxide, or a mixture thereof. A mole ratio of the total amount of the alkali metal hydroxide and the alkaline-earth metal hydroxide to the amount of the 17β-[(N,N-dimethyl carbamoyl)thio]carbonyl compound may be about 1:1 to about 5:1. The mole ratio of the total amount of the alkali metal hydroxide and the alkaline-earth metal hydroxide to the amount of the 17β-[(N,N-dimethyl carbamoyl)thio]carbonyl compound may be about 1.5:1. The alcohol may include any suitable alcohol, such as methanol, ethanol, propanol, butanol, or a mixture thereof.

The acid may include any suitable acid, such as an organic acid, an inorganic acid, or a mixture thereof. The inorganic acid may include hydrochloric acid, phosphoric acid, sulphuric acid, or a mixture thereof. The organic acid may include acetic acid, formic acid, propionic acid, or a mixture thereof. The acid may be added to the aqueous portion to obtain a pH of 1 to 5. For example, the acid may be added to the aqueous portion to obtain a pH of 2 to 3.

The treating of the 17β-[(N,N-dimethyl carbamoyl)thio]carbonyl compound (e.g., Compound 4) may be performed at a reaction temperature of about 0° C. to about 50° C. For example, the reaction temperature may be about 25° C. to about 30° C. A volume to weight ratio of the volume of the alcohol to the weight of the 17β-[(N,N-dimethyl carbamoyl)thio]carbonyl compound (e.g., Compound 4) may be about 5:1 to 30:1 v/w. For example, the volume to weight ratio of the alcohol to the 17β-[(N,N-dimethyl carbamoyl)thio]carbonyl compound may be about 15:1 v/w.

In other processes in which Compound 4 is decomposed to form diethylamine and a thioic acid (Compound 1), diethylamine functions as a solvent and a reagent. After the reaction (the decomposition), hydrochloric acid is added for neutralization, which generates substantial amounts of organic waste water containing diethylamine, and the percent yield (actual yield theoretical yield) of the final product yield is only about 40%. Therefore, the addition of more agents (e.g., diethylamine) results in more pollution and the yield of such a diethylamine based process is low, as compared to embodiments of the present disclosure.

Embodiments of the present disclosure utilize methane as a solvent. Methane may be distilled for recycling, which may effectively reduce the amount of organic waste (or organic wastewater) produced. Additionally, according to embodiments of the present disclosure, the percent yield of Compound 1 is improved by up to 100% (i.e., from 45% to 90%), as compared to other processes. Therefore, embodiments of the process disclosed herein utilize fewer agents (or smaller amounts of agents) and are relatively environmentally friendlier. Additionally, the yield of fluticasone propionate is greatly increased.

In methods that utilize a hydrolyzing agent, such as sodium hydrosulfide or sodium thiomethoxide, an excess amount of the hydrolyzing agent may generate toxic hydrogen sulfide or methyl mercaptan. If the alkylation of the sodium salt of Compound 1 is direct, excess sodium hydrosulfide may react with chlorofluoromethane, and thus, more chlorofluoromethane may be required (e.g., to compensate for the chlorofluoromethane that reacts with the excess sodium hydrosulfide). Further, the resultant impurity of such processes is difficult to remove, which may affect (or reduce) the quality (or purity) of the final product. Embodiments of the present disclosure avoid or reduce the generation of toxic hydrogen sulfide or methyl mercaptan, the need for additional chlorofluoromethane, and the generation of difficult-to-remove impurities.

Embodiments of the presently disclosed method do not generate the impurity carboxylic acidmethyl ester, thereby rendering the treatment simpler and the purity of Compound 1 relatively higher (e.g., higher than 98%).

Figure 2:
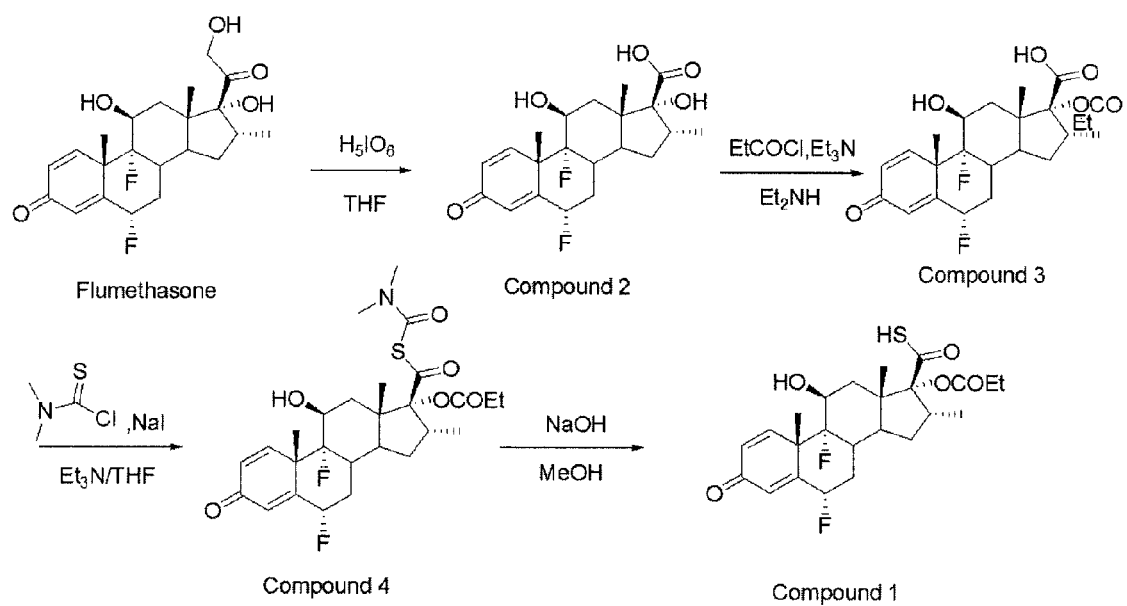
FIG. 2 is a reaction scheme illustrating a synthetic route of an embodiment of a method of preparing a thioic acid intermediate of fluticasone propionate according to Reaction Scheme 1.

A synthesis route according to an embodiment of the present disclosure is shown in Reaction Scheme 1 of FIG. 2.

In FIG. 2, Compound 2 is prepared by the oxidation of flumethasone with an oxidizing agent. The oxidizing agent may include per-iodic acid (e.g., orthoperiodic acid ($H_5IO_6$), metaperiodic acid ($HIO_4$), or mixture thereof) in tetrahydrofuran (THF). Compound 2 is then reacted to form Compound 3, for example, by reacting Compound 2 in the presence of or with propionyl chloride and catalysts (e.g., triethylamine and/or dimethylamine in acetone) to aminolyze Compound 2 and obtain Compound 3. Compound 3 is then reacted to obtain Compound 4. For example, Compound 3 may be reacted in the presence of or with N,N-dimethylthiocarbamoyl chloride, sodium iodide and triethylamine as catalysts in tetrahydrofuran to obtain Compound 4. Compound 4 is reacted with an alkali metal hydroxide, such as sodium hydroxide, and/or an alkaline-earth metal hydroxide, such as calcium hydroxide, in alcohol, such as methanol, to obtain Compound 1.

A process of using alkali metal carbonate/alcohol has also been used for the preparation of Compound 1. Although such a method can provide an improved yield of Compound 1, a methyl ester impurity is generated by that method, and the methyl ester impurity is difficult to remove, which affects (or reduces) the quality (or purity) of the final product. A process of using alkali metal phosphate/alcohol has also been used, but it too has been observed to produce a difficult-to-remove impurity in the process.

EXAMPLES

The following examples provide further details of certain embodiments of the current disclosure. The examples are provided to illustrate embodiments of the present disclosure, but the present invention is not limited thereto. Certain features of the reaction scheme of FIG. 2 are embodied in the following examples:

Example 1

Compound 2, i.e., 6α,9α-difluoro-11β-hydroxy-16α-methyl-3-oxoandrosta-1,4-diene-17β-carboxylic acid, was prepared as follows.

A solution of per-iodic acid (36.2 g) in water (72 ml) was prepared. This solution was added dropwise to a stirred suspension of flumethasone (30 g) in tetrahydrofuran (150 ml) at a temperature of 0 to 10° C. to form a reaction solution. After completion (or substantial completion) of the addition of the solution of per-iodic acid, the reaction solution was stirred further for 2 hours. Tetrahydrofuran was then evaporated (at least a substantial portion of the tetrahydrofuran was evaporated), the resultant solution was cooled to a temperature of 0 to 10° C., and the resultant solution was maintained at a temperature of 0 to 10° C. for 2 hours and then filtered to obtain a filtered product. The filtered product was washed with water and dried at 50° C. to obtain a final product. 28.3 g of the final product having a purity of 99.5% (the final product included 99.5 wt % of Compound 2 based on the total weight of the final product) was obtained. The percent yield of Compound 2 was 98.2%. The percent yield of Compound 2 was calculated as shown in Equation 1. The percent yield in each of Examples 2 to 5 was calculated in a similar manner.

$$\text{Percent yield} = \frac{(\text{Weight of Compound 2} \div \text{molecular weight of Compound 2}) * \text{Purity \%}}{(\text{Weight of flumethasone} \div \text{molecular weight of flumethasone}) * \text{Purity \%}} \qquad \text{Equation 1}$$

$$\text{Percent yield} = \frac{(28.3 \text{ g} \div 396.42 \text{ g/mol}) * 99.5\%}{(30 \text{ g} \div 410.45 \text{ g/mol}) * 99\%} = 98.2\%$$

Example 2

Compound 3, i.e., 6α,9α-difluoro-11β-hydroxy-16α-methyl-3-oxo-17α-propionyoxyandrosta-1,4-diene-17β-carboxylic acid, was prepared as follows.

40 ml of triethylamine was added to a suspension including Compound 2 (50 g, 99.5 wt %, in 250 ml of acetone) at a temperature of 0 to 10° C. to prepare a reaction solution. Then, 45.6 ml of propionyl chloride was added to the reaction solution. After completion (or substantial completion) of the addition, the reaction solution was stirred for 1 hour. Diethylamine (50 ml) was then added to the reaction solution, which was then stirred for 2 hours to form a reaction mixture. Thereafter, the reaction mixture was acidified to a pH of about 1 to 2 by adding 2M hydrochloric acid to form a precipitated product. The precipitated product was filtered, washed with water, and dried at 50° C. to obtain a final product. 54.5 g of the final product having a purity of 99.2% (the final product included 99.2 wt % of Compound 3 based on the total weight of the final product). The percent yield of Compound 3 was 98.6%.

Example 3

Compound 4, i.e., 17β-[(N,N-dimethylcarbamoyl)thio]carbonyl-6α,9α-difluoro-11β-hydroxy-16α-methyl-3-oxo-17α-propionyloxyandrosta-1,4-diene, was prepared as follows.

A solution of Compound 4 (31 g, 99.2 wt %) in tetrahydrofuran (240 ml) was stirred at room temperature, and dimethylthiocarbamoyl chloride (18.3 g), sodium iodide (3.0 g) and triethylamine (20 ml) were added thereto and the resultant was stirred for 16 hours. Then, the resultant was treated with N,N-dimethylformamide (90 ml) and water (600 ml) to prepare a mixture. The mixture was cooled to a temperature of 0 to 10° C., and stirred for 2 hours. The resultant product was filtered, washed with water and dried at 50° C. to obtain a final product. 36.1 g of the final product having a purity of 98.8% (the final product included 98.8% of Compound 4 based on the total weight of the final product) was obtained. The percent yield of Compound 4 was 97.3%.

Example 4

Compound 1, i.e., 6α,9α-difluoro-11β-hydroxy-16α-methyl-3-oxo-17α-propionyloxyandrosta-1,4-diene-17β-carbothioate, was prepared as follows.

A suspension including 35 g of Compound 4 (98.8 wt %) and 3.9 g of sodium hydroxide in 525 ml of methanol was stirred at a temperature of 25 to 30° C. for 24 hours. The methanol was then evaporated from the suspension (at least a substantial portion of the methanol was evaporated). Thereafter, 140 ml of acetic ether (ethyl acetate) and 350 ml water were added thereto, and the resultant was stirred for 30 minutes and an aqueous solution was separated therefrom. Thereafter, the aqueous solution was acidified to a pH of about 2 to 3 by adding 2M hydrochloric acid dropwise to the aqueous solution to obtain a precipitated product. The precipitated product was filtered, washed with water, and dried at 50° C. to obtain a final product. 29.2 g of the final product having a purity of 98.5% (the final product included 98.5 wt % of Compound 1 based on the total weight of the final product) was obtained. The percent yield of Compound 1 was 95.8%.

Example 5

A suspension including 30 g of Compound 4 (98.8 wt %), and 6.2 g of calcium hydroxide in 450 ml methanol were stirred at a temperature of 25 to 30° C. for 24 hours. The methanol was then evaporated from the suspension (at least a substantial portion of the methanol was evaporated). Thereafter, 120 ml of acetic ether (ethyl acetate) and 300 ml water were added thereto, and the resultant was stirred for 30 minutes and an aqueous solution was separated therefrom. Thereafter, the aqueous solution was acidified to a pH of about 2 to 3 by 2M hydrochloric acid to obtain a precipitated product. The precipitated product was filtered, washed with water, and dried at 50° C. to obtain a final product. 25.1 g of the final product having a purity of 98.7% (the final product included 98.7 wt % of Compound 1 based on the total weight of the final product) was obtained. The percent yield of Compound 1 was 96.3%.

Compound 1 may then be utilized to obtain fluticasone propionate according to any suitable method in the art. For example, Compound 1 may be alkylated to obtain fluticasone propionate. In some embodiments, Compound 1 is alkylated with a halohydrocarbon. The halohydrocarbon may include a chlorofluorocarbon. For example, the chlorofluorocarbon may include chlorofluoromethane.

While the present invention has been described in connection with certain embodiments, it is to be understood that the invention is not limited to the disclosed embodiments, but, on the contrary, is intended to cover various modifications and equivalent arrangements included within the spirit and scope of the appended claims, and equivalents thereof. Throughout the text and claims, the terms "about" and "substantially" are used as terms of approximation, not terms of degree, and reflect the inherent variation associated with measurement, significant figures, and interchangeability, all as understood by a person having ordinary skill in the relevant art. Also, it is to be understood that throughout this disclosure and the accompanying claims, even values that are not preceded by the term "about" are also implicitly modified by that term, unless otherwise specified.

What is claimed is:

1. A method of preparing a thioic acid intermediate of fluticasone propionate, the method comprising:
   treating Compound 4, 17β-[(N,N-dimethylcarbamoyl)thio]carbonyl-6α,9α-difluoro-11β-hydroxy-16α-methyl-3-oxo-17α-propionyloxyandrosta-1,4-diene in a solution comprising an alcohol and an alkali metal hydroxide, an alkaline-earth metal hydroxide, or a mixture thereof to cleave an amide from Compound 4;
   treating the solution to separate an aqueous portion; and
   adding an acid to the aqueous portion to obtain the thioic acid intermediate of fluticasone propionate:

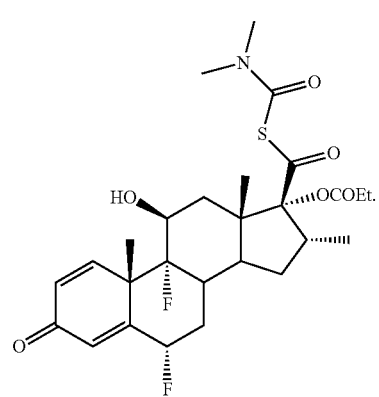

Compound 4

2. The method of claim 1, wherein the thioic acid intermediate of fluticasone propionate is Compound 1, 6α,9α-difluoro-11β-hydroxy-16α-methyl-3-oxo-17α-propionyl oxyandrosta-1,4-diene-17β-carbothioate:

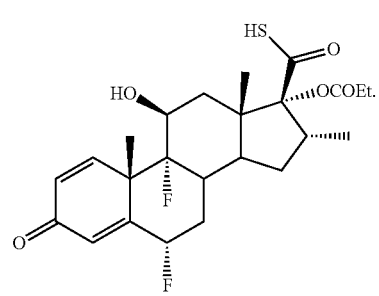

Compound 1

3. The method of claim 1, wherein the treating of the solution removes impurities and comprises evaporating at least a portion of the alcohol, adding water and an organic solvent, and stirring to separate the aqueous portion from the solution.

4. The method of claim 1, wherein the adding of the acid comprises adding the acid dropwise to the aqueous portion.

5. The method of claim 1, wherein the alkali metal hydroxide comprises lithium hydroxide, sodium hydroxide, potassium hydroxide, or a mixture thereof, and
wherein the alkaline-earth metal hydroxide comprises magnesium hydroxide, calcium hydroxide, or a mixture thereof.

6. The method of claim 1, wherein the alkali metal hydroxide comprises sodium hydroxide, and
wherein the alkaline-earth metal hydroxide comprises calcium hydroxide.

7. The method of claim 1, wherein the mole ratio of the total amount of the alkali metal hydroxide and the alkaline-earth metal hydroxide to the amount of Compound 4 is about 1:1 to about 5:1.

8. The method of claim 7, wherein the mole ratio of the total amount of the alkali metal hydroxide and the alkaline-earth metal hydroxide to the amount of Compound 4 is about 1.5:1.

9. The method of claim 1, wherein the alcohol comprises methanol, ethanol, propanol, butanol, or a mixture thereof.

10. The method of claim 9, wherein the alcohol comprises methanol.

11. The method of claim 9, wherein a volume to weight ratio of the alcohol to Compound 4 is about 5:1 to 30:1 v/w.

12. The method of claim 11, wherein the volume to weight ratio of the alcohol to Compound 4 is about 15:1 v/w.

13. The method of claim 1, wherein the treating of Compound 4 is performed at a reaction temperature of about 0° C. to about 50° C.

14. The method of claim 13, wherein the reaction temperature is about 25° C. to about 30° C.

15. The method of claim 3, wherein the organic solvent comprises an ester, an ether, an alkane, an aromatic hydrocarbon, a halohydrocarbon or a mixture thereof.

16. The method of claim 15, wherein the ester comprises ethyl acetate, methyl acetate, butyl acetate, or a mixture thereof.

17. The method of claim 15, wherein the ether comprises diethyl ether, methyl tert butyl ether, or a mixture thereof.

18. The method of claim 15, wherein the organic solvent comprises toluene, dichloromethane, chloroform, or a mixture thereof.

19. The method of claim 15, wherein the aromatic hydrocarbon comprises toluene.

20. The method of claim 1, wherein the acid comprises an organic acid, an inorganic acid, or a mixture thereof.

21. The method of claim 20, wherein the inorganic acid comprises hydrochloric acid, phosphoric acid, sulphuric acid, or a mixture thereof, and
wherein the organic acid comprises acetic acid, formic acid, propionic acid, or a mixture thereof.

22. The method of claim 20, wherein the acid is added to the aqueous portion to obtain a pH of 1 to 5.

23. The method of claim 22, wherein the pH is 2 to 3.

24. A method of preparing fluticasone propionate, the method comprising:
preparing the thioic acid intermediate of fluticasone propionate according to the method of claim 1; and
alkylating the thioic acid intermediate of fluticasone propionate to prepare the fluticasone propionate.

\* \* \* \* \*